United States Patent
Radatti et al.

(10) Patent No.: US 9,689,719 B2
(45) Date of Patent: Jun. 27, 2017

(54) COVER FOR A DUCT SENSOR

(71) Applicant: Siemens Schweiz AG, Zurich (CH)

(72) Inventors: Giuseppe Radatti, Pfaeffikon (CH); Martin Zimmermann, Zwillikon (CH)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 14/856,887

(22) Filed: Sep. 17, 2015

(65) Prior Publication Data

US 2016/0123779 A1    May 5, 2016

(30) Foreign Application Priority Data

Oct. 29, 2014  (EP) ..................... 14190958

(51) Int. Cl.
G01D 11/24    (2006.01)
G01N 27/22    (2006.01)
G01N 27/407   (2006.01)

(52) U.S. Cl.
CPC ....... *G01D 11/245* (2013.01); *G01N 27/4078* (2013.01); *G01N 27/226* (2013.01); *G01N 27/4071* (2013.01); *G01N 27/4077* (2013.01)

(58) Field of Classification Search
CPC ... G01D 11/24; G01N 27/4078; G01N 27/226
USPC ................................. 73/431, 31.01
See application file for complete search history.

(56) References Cited

U.S. PATENT DOCUMENTS

| | | | |
|---|---|---|---|
| 3,175,391 A | 3/1965 | Rudigier, Jr. .................... 73/73 |
| 6,063,249 A | 5/2000 | Duce et al. ................... 204/424 |
| 6,658,933 B2* | 12/2003 | Allegre ............... G01F 23/2927 | 250/357.1 |
| 7,377,149 B2* | 5/2008 | Ruth .................... G01N 27/407 | 204/424 |
| 8,567,234 B2* | 10/2013 | Fujita ................. G01N 27/4077 | 73/23.2 |
| 2003/0061862 A1* | 4/2003 | Kondo ............... G01N 27/4077 | 73/23.31 |

(Continued)

FOREIGN PATENT DOCUMENTS

| | | | | |
|---|---|---|---|---|
| CH | EP 1577648 A1 * | 9/2005 | .......... G01D 11/245 |
| EP | 1577648 B1 | 8/2006 | ............. G01D 11/24 |

(Continued)

OTHER PUBLICATIONS

Russian Office Action, Application No. 2015145769/15, 2 pages, Feb. 14, 2017.

*Primary Examiner* — Lisa Caputo
*Assistant Examiner* — Jamel Williams
(74) *Attorney, Agent, or Firm* — Slayden Grubert Beard PLLC

(57) ABSTRACT

A cover for a duct sensor includes an outer envelope extending circumferentially around the cover, a seal projecting from the outer envelope and extending circumferentially around the outer envelope, a duct extending through the cover and defining a plurality of walls including side walls, and a front surface connecting to the outer envelope and to the walls of the duct. A guide runner is laterally arranged along a side wall of the duct. An opening in the front surface of the cover provides an entry for a circuit board into the duct, and the guide runner is configured to support a circuit board extending through the duct.

13 Claims, 4 Drawing Sheets

(56) References Cited

U.S. PATENT DOCUMENTS

| | | | |
|---|---|---|---|
| 2006/0162423 A1* | 7/2006 | Ruth | G01N 27/4078 73/23.31 |
| 2007/0012087 A1* | 1/2007 | Ruth | G01N 27/407 73/31.01 |
| 2009/0266183 A1* | 10/2009 | Hall | F24F 11/0017 73/865.9 |
| 2014/0144243 A1* | 5/2014 | Tanaka | G01L 13/025 73/716 |
| 2015/0137980 A1* | 5/2015 | Hatsir | G08B 17/04 340/584 |
| 2015/0260698 A1* | 9/2015 | Hirata | G01M 15/102 73/23.31 |

FOREIGN PATENT DOCUMENTS

| | | | | |
|---|---|---|---|---|
| JP | EP 1167958 A1 * | 1/2002 | | G01N 27/4077 |
| RU | 114152 U1 | 3/2012 | | G01L 19/00 |

* cited by examiner

COVER FOR A DUCT SENSOR

CROSS-REFERENCE TO RELATED APPLICATIONS

This application claims priority to EP Application No. 14190958.0 filed Oct. 29, 2014, the contents of which are hereby incorporated by reference in their entirety.

TECHNICAL FIELD

The present disclosure is about a cover for a duct sensor. The present disclosure focuses on a cover for a duct moisture sensor wherein the cover provides a duct.

BACKGROUND

Duct sensors are commonly used to sense environmental conditions such as temperature and/or humidity. They may, for instance, be employed in installations for heating, ventilation, and/or air conditioning. Commercial, industrial and/or residential sites typically provide such installations with duct sensors.

A typical duct sensor comprises a tubular housing and an elongated circuit board arranged inside the housing. The circuit board inside the tubular housing may provide an electric and/or an electronic circuit to process and to analyze signals obtained from a sensor. The printed circuit board may extend outside the tubular housing.

A cover is commonly employed to separate sections of the same (printed) circuit board inside and outside the tubular housing. The cover typically provides a duct such that the elongated circuit board passes through the cover. The duct also seals the elements of the sensor inside the tubular housing against ingress of fluids such as moisture. In doing so, the duct acts to protect the elements on the inside of the housing against corrosion.

To further protect against corrosion, the inside of the housing may be filled with a suitable moisture-impervious potting compound. By protecting the circuit inside the housing against ingress of fluids, any adverse influence of moisture on electric and/or electronic elements of the sensor is minimized. The moisture-impervious potting compound may also fill and/or impregnate any voids inside the protected part of the sensor, thereby enhancing electrical insulation inside the housing.

The U.S. Pat. No. 3,175,391 was granted in 1965 and discloses a humidity measuring device for measuring moisture in stacks of sheet material, such as stacks of paper. FIG. 1 of U.S. Pat. No. 3,175,391 shows a module assembly 18 arranged inside a housing 22. Apertures 23 are provided at one end of the housing 22 such that air may circulate through the apertures 23 into the housing 22. The module assembly 18 operates to sense humidity. Consequently, the module assembly 18 is arranged inside the housing 22 and in the vicinity of the apertures 23.

A terminal block 16 separates the end of the housing 22 with the apertures 23 from the other end of the housing. On the opposite side of the terminal block 16, various resistors R3, R4 act to process and analyze the signal from the humidity sensor. The resistors R3, R4 are arranged inside a notch 14 where they are cast in a suitable potting compound.

FIG. 9 of U.S. Pat. No. 3,175,391 shows the terminal block 16 and how it 16 is mounted to the housing 22. FIG. 9 and FIG. 4 depict two side lugs 43, one fastening member 19, 20 for each lug 43 and a finger 15 adjacent to the lugs 43. Each of the fastening members 19, 20 extends through one of the lugs 43. FIG. 11 shows that the fastening member 19 is engaged on the finger 15 through a threaded connection. Likewise, FIG. 9 shows the fastening member 20 engaged on a stud 60 mounted to the same finger 15.

The patent application US2007/0012087A1 was filed on 9 Feb. 2004. US2007/0012087A1 teaches a sensor.

The patent US006063249A issued on 16 May 2000. US006063249A discloses an oxygen sensor.

SUMMARY

One embodiment provides a cover for a duct sensor comprising an outer envelope circumferentially surrounding the cover and connecting to at least one seal, the at least one seal standing proud of the outer envelope and circumferentially surrounding the outer envelope; at least one duct with walls and with side walls, the at least one duct extending through the cover; a front surface connecting to the outer envelope and to the walls of the at least one duct; wherein the at least one duct comprises at least one guide runner laterally arranged along a side wall of the duct; wherein the cover comprises an opening in the front surface; wherein the opening provides an entry for a circuit board into the at least one duct; wherein the at least one guide runner is configured to support a circuit board extending through the duct; wherein the at least one guide runner and the opening are configured to substantially prevent play of a circuit board extending through the duct; wherein the at least one seal comprises a tip, and the at least one seal and the tip and the outer envelope and the cover form a single piece.

In a further embodiment, the opening is rectangular and/or wherein the width of the opening and/or the height of the opening are such that a circuit board may fit through the opening.

In a further embodiment, the at least one seal is configured to mate with a flat surface or with a reciprocating groove in an inner wall of a tubular housing such that the arrangement becomes fluid-tight.

In a further embodiment, the at least one seal and the tip and the outer envelope and the cover are made of the same material.

In a further embodiment, the outer envelope and/or the at least one seal and/or the tip all have cylindrical symmetry with respect to an axis through the at least one duct.

In a further embodiment, the at least one seal is resiliently yieldable so as to adapt to a groove on the inside of a tubular housing.

In a further embodiment, the at least one seal is an annular seal and/or wherein the at least one seal is configured to mate with an annular groove on the inside of a tubular housing.

In a further embodiment, the at least duct provides guide runners on either side wall of the at least one duct.

In a further embodiment, the opening provides at least one lip and the at least one lip is configured to mate with a reciprocating groove in the surface of a circuit board such that the arrangement becomes fluid-tight.

In a further embodiment, the opening provides at least one lip and the at least one lip is configured to snugly receive the surface of a circuit board such that the arrangement becomes fluid-tight.

In a further embodiment, a plurality of apertures, e.g., four apertures, are arranged in the front surface of the cover.

Another embodiment provides a duct sensor comprising a tubular housing with end portions, a circuit board, and a cover as disclosed above, wherein the cover is mounted inside the tubular housing, and wherein the circuit board extends through the cover.

In a further embodiment, the end portions provide inner surfaces and wherein the front surface of the cover is flush with inner surfaces of the end portions.

In a further embodiment, the cover connects to the walls of the tubular housing such that no uncured potting compound will leak in between the cover and the tubular housing.

In a further embodiment, the cover connects to the circuit board such that no uncured potting compound will leak in between the cover and the tubular housing.

BRIEF DESCRIPTION OF THE DRAWINGS

Example embodiments are discussed below with reference to the drawings, in which.

DETAILED DESCRIPTION

Embodiments of the present disclosure provide a cover for a tubular housing without threaded connections. The corresponding sensor may also meet other technical requirements as set out above, especially tightness, protection of electric and/or electronic circuits, and insulation.

Some embodiments provide a cover for the tubular housing of a duct sensor. The cover shall provide a duct such that a circuit board, in particular a printed circuit board, may extend through the duct. The duct shall seal the inside of the housing of the sensor against ingress of moisture and/or fluids. Also, the duct shall seal the sensor such that no uncured potting compound will leak from the arrangement. To that end, the duct shall snugly surround any circuit board extending through the duct.

No threaded or bolted connection shall be required to mount the duct to the tubular housing of a sensor. No design of a specialized tool shall be required for the purpose of mounting the cover to the tubular housing.

The cover for the tubular housing of a duct sensor and the sensor itself shall comprise relatively few parts, be inexpensive to manufacture, especially adapted for economical manufacture by mass production, durable in construction, responsive to a wide range of moisture conditions, and suitable for use in a heating, ventilation, air-conditioning system.

The above problems are resolved by a cover for a tubular housing of a duct sensor according to the main claim(s) of this disclosure. Preferred embodiments of the present disclosure are covered by the dependent claims.

In other words, the instant disclosure teaches a cover for a duct sensor comprising an outer envelope circumferentially surrounding the cover and connecting to at least one seal, the at least one seal standing proud of the outer envelope and circumferentially surrounding the outer envelope, at least one duct with walls and with side walls, the at least one duct extending through the cover, a front surface connecting to the outer envelope and to the walls of the at least one duct, wherein the at least one duct comprises at least one guide runner laterally arranged along a side wall of the duct, wherein the cover comprises an opening in the front surface, wherein the opening provides an entry for a circuit board into the at least one duct, wherein the at least one guide runner is configured to support a circuit board extending through the duct, wherein the at least one guide runner and the opening are configured to substantially prevent play of a circuit board extending through the duct.

Other embodiments provide a duct sensor, in particular a duct moisture sensor, with the aforementioned cover.

Other embodiments provide a heating, ventilation, and/or air conditioning system with the aforementioned sensor.

Figure 1:
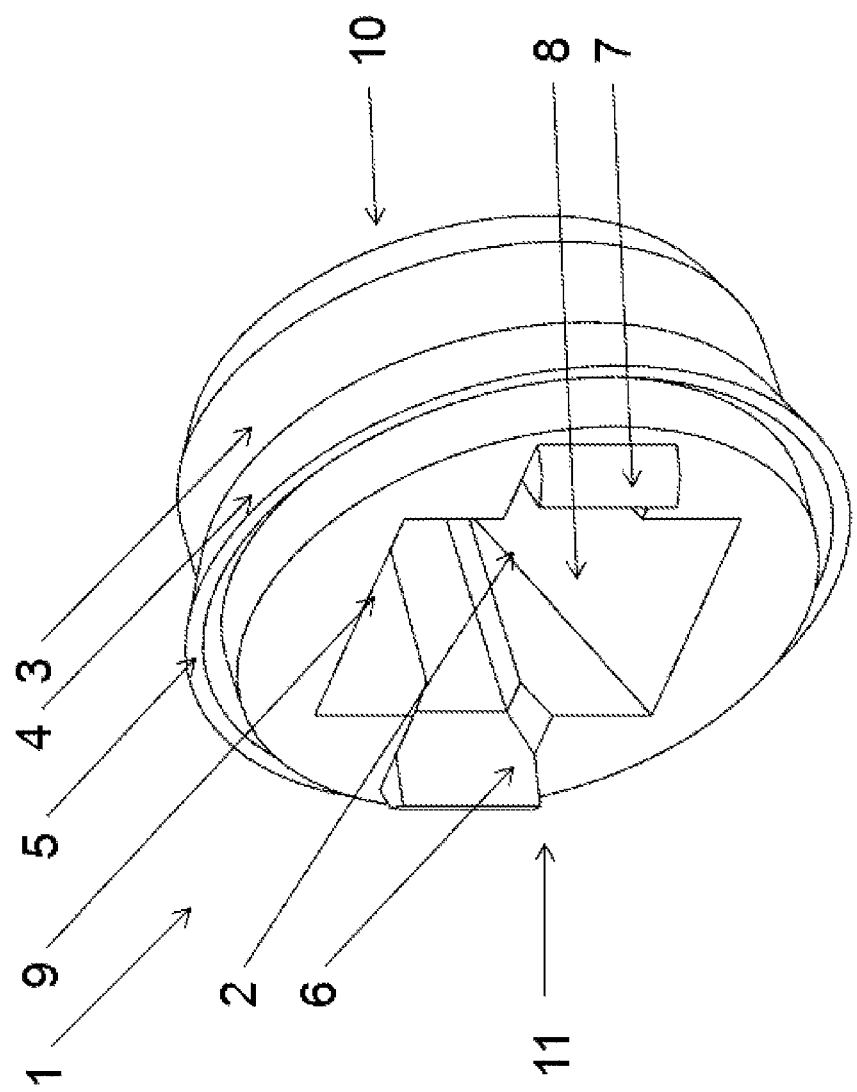
FIG. 1 is a rear view of the cover for a tubular housing of a duct sensor.

FIG. 1 shows a cover 1 according to one embodiment. A duct 2 with walls 8, 9 extends through the cover 1 and is adapted such that a circuit board laterally fits between the walls of the duct 2. The duct 1 has an outer envelope 3. In a preferred embodiment, the outer envelope 3 has cylindrical symmetry. It is envisaged that the outer envelope 3 has cylindrical symmetry and that a symmetry axis of the outer envelope 3 extends through the duct 2.

The cover 1 also provides a seal 4. The (annular) seal 4 is adapted to mate with an (annular) groove on the inside of a tubular housing. The sealing element 4 circumferentially surrounds the outer envelope 3 of the duct 2. The sealing element 4 tapers toward the front end 10 with a front surface of the cover 1. It 4 terminates in the outer envelope 3.

In other words, the instant disclosure teaches a cover 1, wherein the at least one seal 4 is an annular seal 4 and/or wherein the at least one seal 4 is configured to mate with an annular groove on the inside of a tubular housing 18.

The tip 5 at the far end of the sealing element is part of the sealing element 4 and is arranged at a small distance from the outer envelope 3 of the cover 1. The gap in between the tip 5 of the sealing element 4 and the outer envelope 3 allows for a resiliently yieldable sealing element 4. The yieldable sealing element 4 can thus adapt to a groove on the inside of a tubular housing. The groove may, in particular, vary in size and in its surface may be uneven to some extent. Further, minor deviations of the groove from cylindrical symmetry may be tolerated.

In other words, the instant disclosure teaches a cover 1, wherein the at least one seal 4 is resiliently yieldable so as to adapt to a groove on the inside of a tubular housing 18.

It is envisaged that the sealing element 4 and the outer envelope 3 both have cylindrical symmetry. It is further envisaged that the sealing element 4 and the outer envelope 3 have the same symmetry axis.

According to one embodiment, the tip 5 and the cover 1 form a single piece. The tip 5 and the cover 1 may be made of a suitable polymeric material. The material shall preferably be durable in the long term. In a preferred embodiment, the tip 5 may be made of a vulcanizing polymer such as Santoprene™. In an alternate embodiment, the cover 1 and the tip 5 are made of flexible epoxy. The skilled person may also select other suitable materials for the cover 1.

FIG. 1 also shows the seal 4 with its tip 5 stands proud of the outer envelope 3. In a particular embodiment, the outer surface of the seal 4 and the outer envelope 3 form an acute angle between 10 degrees and 40 degrees, more preferable between 15 degrees and 30 degrees, yet more preferable between 20 and 25 degrees. This angle may actually vary under the influence of external forces applies to the resiliently yieldable seal 4.

It is also envisaged that the cover 1 may provide two latching members 6, 7. The members 6, 7 act to laterally latch onto suitable notches along the side edges of a circuit board, thereby fixating the circuit board. According to a preferred embodiment, the latching members 6, 7 and the cover 1 form a single piece. The latching members 6, 7 and the cover 1 may, in particular, all be made of the same material.

In other words, the instant disclosure teaches a cover 1, wherein the at least one seal 4 and the tip 5 and the outer envelope 3 and the cover 1 form a single piece (that is, they form a single-piece design) and/or wherein the at least one seal 4 and the tip 5 and the outer envelope 3 and the cover 1 are made of the same material.

The instant disclosure also teaches a cover 1, wherein the outer envelope 3 and/or the at least one seal 4 and/or the tip 5 all have cylindrical symmetry with respect to an axis through the at least one duct 2.

According to a particular embodiment, at least one wall 8 of the duct 2 is arranged at an angle. According to another embodiment, at least two walls 8, 9 of the duct 2 are arranged at an angle and/or form tapered surfaces. FIG. 1 shows that the bottom wall 8 and the top wall 9 are not parallel. In other words, the duct 2 through the cover 1 provides an aperture for receiving a circuit board and that aperture narrows toward the front end 10 of the cover 1.

In a particular embodiment, the top wall 9 and the bottom wall 8 are arranged at an angle between 40 degrees and 90 degrees, more preferable between 50 degrees and 80 degrees, yet more preferable at an acute angle of 65 or of 55 degrees.

In one embodiment, the length of the cover 1 between its front end 5 and its rear end 11 is between 2 and 9 millimeters, more preferred between 3 and 7 millimeters, yet more preferred between 3 and 5 millimeters.

It is envisaged that the width of the cover 1 between opposite ends of the seal 4 lies between 5 and 15 millimeters, more preferably between 7 and 12 millimeters, yet more preferably between 9 and 10 millimeters.

It is also envisaged that the ratio between the width and the length of the cover 1 is between 2 and 4, more preferred between 2.5 and 3, yet more preferred 2.66 or 2.8.

Figure 2:
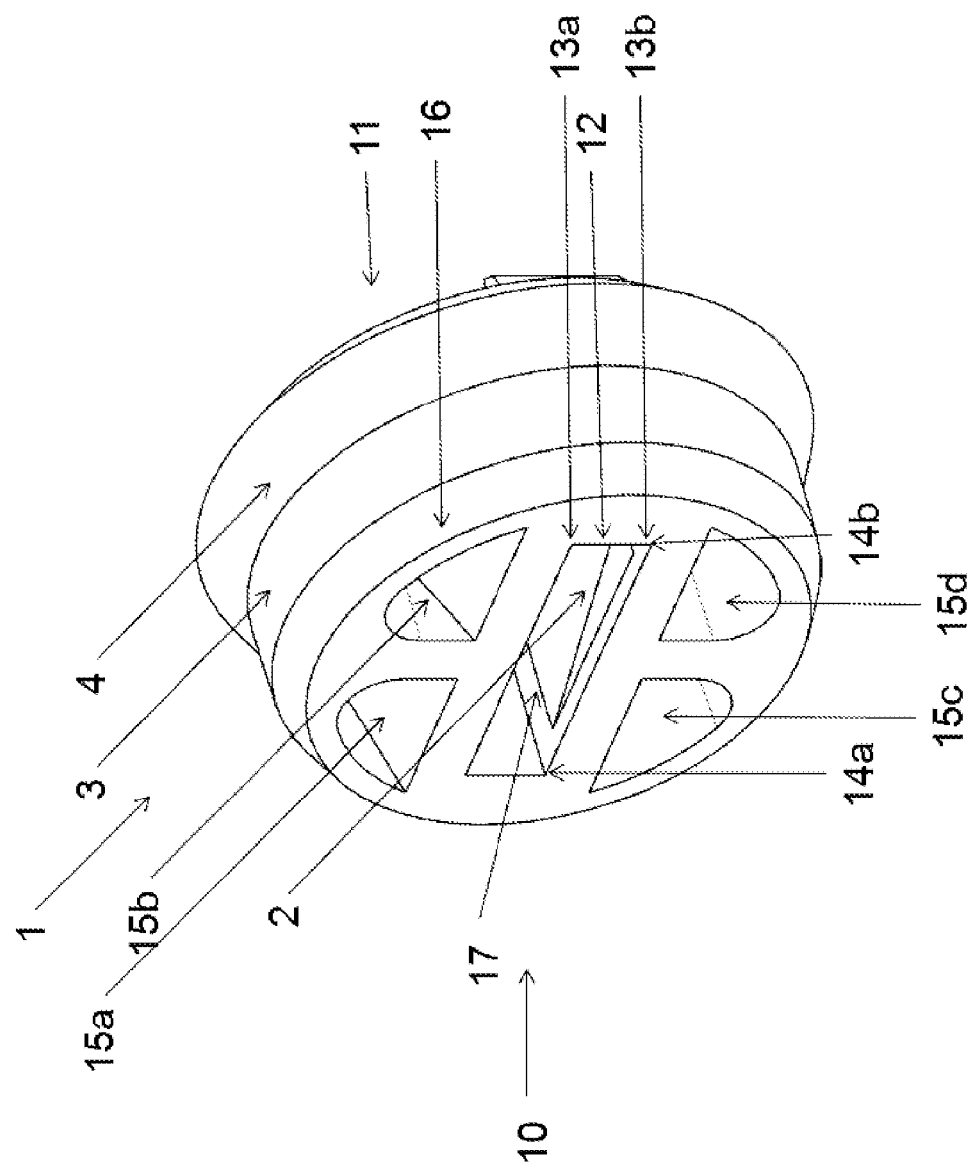
FIG. 2 is a front view of the cover for a tubular housing of a duct sensor.

FIG. 2 shows the same cover 1, the same outer envelope 3, the same sealing element etc as FIG. 1. The main difference between the FIG. 1 and FIG. 2 is that FIG. 2 shows the cover 1 from its front. By contrast, FIG. 1 provides a rear view of the cover 1.

The cover 1 as shown on FIG. 1 provides a rectangular opening 12 at its 1 front end 10. The opening 12 thus is an opening 12 in the front surface of the cover 1 such that a circuit board may penetrate the front surface and enter the duct 2. The rectangular opening 12 is especially adapted to receive a (printed and/or elongated) circuit board. The height of the rectangular opening 12 along the axis 13a, 13b therefore is between 1 and 2.5 millimeters, preferably 1.1 millimeters or 1.2 millimeters or 1.3 millimeters or 1.4 millimeters or 1.5 millimeters or 1.8 millimeters or 1.9 millimeters or 2.0 millimeters or 2.1 millimeters or 2.2 millimeters. It is envisaged that the rectangular opening 12 is wider at its entry 10 than inside the duct 2 and narrows toward the rear end 11 of the duct 2. Consequently, it will be less difficult to insert a (printed) circuit board into the rectangular opening 12.

In other words, the instant disclosure teaches a cover 1, wherein the opening 12 is rectangular and/or wherein the width of the opening 12 and/or the height of the opening 12 are such that a circuit board 20 may fit through the opening 12.

The width of the rectangular opening 12 along the axis 14a, 14b is between 3 and 10 millimeters, more preferred between 3 and 8 millimeters, yet more preferred between 4 and 6 millimeters.

The skilled person readily understands that tolerances apply to the dimensions of the cover 1 and to the choices of materials for the cover 1.

In a particular embodiment, a plurality of apertures 15a, 15b, 15c, 15d are arranged in the front surface at the front end 10 of the cover 1. The cover 1 preferably comprises between 2 and 6 such apertures. Yet more preferably, the cover 1 comprises 4 such apertures. Typically, the diameter of these apertures is less than a millimeter. The cross-sections of the apertures 15a, 15b, 15c, 15d may be quadratic, rectangular, triangular, oval, circular in shape or any combinations thereof. The cross-section of the apertures may, in particular, take on a shape as shown on FIG. 2. The apertures 15a, 15b, 15c, 15d reduce to the overall stiffness of the cover 1. The apertures 15a, 15b, 15c, 15d thereby make the cover 1 suitable for terminating a wide range of tubular housings. It is envisaged that the apertures 15a, 15b, 15c, 15d are actually recesses. In other words, the apertures 15a, 15b, 15d need not extend through the cover 1.

In other words, the instant disclosure teaches a cover 1, wherein a plurality of apertures 15a, 15b, 15c, 15d is, preferably four apertures 15a, 15b, 15c, 15d are, arranged in the front surface of the cover 1.

The outer envelope 3 provides a tapered end 16 toward the front end 10 of the cover 1. The tapered end 16 reduces the effort involved in fitting the cover 1 to a tubular housing.

It is also envisaged that the duct 2 provides side walls and lateral guide runners 17. The guide runners 17 are laterally arranged along opposite side walls of the duct 2. Ideally, there will be lateral guide runners 17 along either of the two side wall of the duct 2. The lateral guide runners 17 act to fixate the position of a(n elongated) circuit board extending through the duct 2. The lateral guide runners 17 also act to limit and/or to (substantially) prevent play of a (printed) circuit board inside the duct 2.

In other words, the instant disclosure teaches a cover 1, wherein the at least duct 2 provides guide runners 17 on either side wall of the at least one duct 2.

It is envisaged that the guide runners (17) all have the same width. In a particular embodiment, the guide runners (17) are between 0.3 and 0.9 mm in width, preferred between 0.4 and 0.7 mm in width, yet more preferred 0.55 or 0.65 mm in width.

Figure 3:
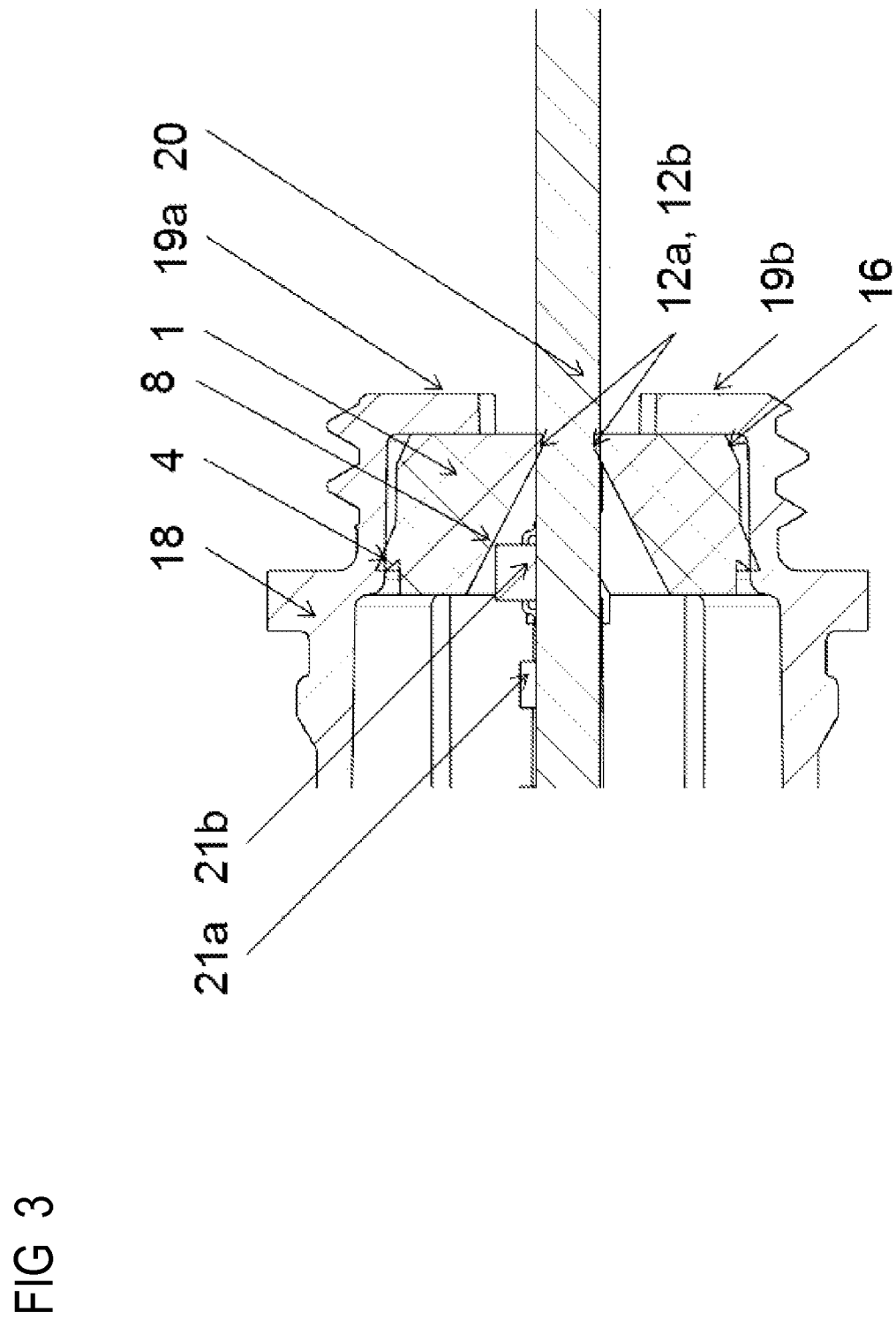
FIG. 3 is a cross-sectional view of an assembly comprising a tubular housing, the cover and a circuit board.

Now turning to FIG. 3, a tubular housing 18 with a cover 1 is fitted to the tubular housing 18. The tubular housing 18 of FIG. 3 comprises end portions 19a, 19b. It is envisaged that the tubular housing 18 forms a single piece together with the end portions 19a, 19b. The front end of the cover 1 is fitted to the tubular housing 18 such that the front surface of the cover 1 is flush with the inner surfaces of the end portions 19a, 19b.

The position of the cover 1 relative to the tubular housing 18 may be defined by the seal 4. The seal 4 then mates with a flat surface or with (a) reciprocating groove(s) in the inner wall of the tubular housing 18. The cover 18 is thus prevented from moving along the inside the tubular housing 18.

FIG. 3 shows a (printed) circuit board inserted 20 into the cover 1. The printed circuit board 20 may have a number of electric and/or electronic components 21a, 21b mounted on its surface. It is also envisaged that surface-mounted devices (SMD) may be arranged on the (printed) circuit board 20. The skilled person will readily understand that the (printed) circuit board 20 of FIG. 3 may as well be replaced by a laminate or by a sheet or similar with suitable dimensions.

In one embodiment, the rectangular opening 12 of the cover 1 mates with especially adapted grooves on the surface of a (printed) circuit board 20. In particular, opposite lips 12a, 12b of the rectangular opening 12 may mate with especially adapted grooves on the surface of a (printed) circuit board 20. One or two walls of the rectangular opening 12 may, by way on non-limiting example, mate with the grooves on the surface of a printed circuit board.

In other words, the instant disclosure teaches a cover 1, wherein the opening 12 provides at least one lip 12a, 12b and the at least one lip 12a, 12b is configured to snugly receive the surface of a circuit board 18 such that the arrangement becomes fluid-tight.

It is envisaged that the cover 1 and the (printed) circuit board 20 as well as the tubular housing 18 are part of a duct sensor. It is further envisaged that the cover 1 connects to the walls of the tubular housing 18. In particular, the seal 4 will connect to the walls of the tubular housing 18 and/or the front surface of the cover 1 will connect to the inner surfaces of the end portions 19a, 19b. It is an object of any of these connections that no uncured potting compound may leak in between the cover 1 and the tubular housing 18.

In other words, the instant disclosure teaches a cover 1, wherein the opening 12 provides at least one lip 12a, 12b and the at least one lip 12a, 12b is configured to mate with a reciprocating groove in the surface of a circuit board 20 such that the arrangement becomes fluid-tight.

It is also envisaged that the cover 1 connects to the surface of the (printed) circuit board 20. In particular the lips 12a, 12b of the rectangular opening 12 will connect to the surface of the circuit board 20. It is an object of any of these connections that no uncured potting compound may leak in between the cover 1 and the circuit board 20.

The cross-section of the tubular housing 18 taken perpendicular to an axis defined by the circuit board 20 is preferably circular. That is, the tubular housing 18 has cylindrical symmetry. In an alternate embodiment, the cross-section of the tubular housing 18 may as well be oval, rectangular, quadratic or any suitable combination thereof. The skilled person chooses a shape of the cover 1 in accordance with the geometry of the tubular housing 1.

The tubular housing 18 may be made of any suitable material such as metallic materials and/or polymeric materials. In a particular embodiment, the tubular housing 18 is made of (stainless) steel. The tubular housing 18 may, in particular, be made of austenitic or ferritic steel. In an alternate embodiment, the tubular housing 18 may as well be made of a polymeric material such as epoxy, polyurethane, polyester, PETP and/or any suitable combination thereof and/or any glass-fiber reinforced formulation of these materials. This list of materials is by way of non-limiting example and is not exhaustive. The skilled person selects a material for the tubular housing 18 that is compatible with the material for the cover 1.

It is envisaged that the cover 1 is fitted to the tubular housing 18 in a manner such that the arrangement becomes fluid-impervious.

To that end, the front surface of the cover 1 is flush with the end portions 19a, 19b of the tubular housing 18. The front surface of the cover 1 connects to the outer envelope 3 of the cover. The front surface also connects to the walls of the duct 2. The skilled person chooses tolerances of the flush-mounted parts to minimize the risk of leakage. Likewise, the seal 4 mates with (a) reciprocating groove(s) on the inner wall of the tubular housing 18.

Likewise, the rectangular opening 12 of the cover 1 snugly receives the (printed) circuit board 20 or lamination. The skilled person chooses materials dimensions and tolerances such that no leakage will occur in between the circuit board 20 or lamination and the cover 1.

It follows that the front surface of the cover 1, the seal 4 and/or the rectangular opening 12 act to ensure the arrangement is fluid-tight. The skilled person readily understands that tightness depends on the type and, in particular, on the viscosity of the fluid. It is envisaged that the arrangement is impervious to fluids with dynamic viscosities between 1 and 100'000 milliPascal·sec, preferably between 10 and 50'000 milliPascal·sec, yet more preferably between 100 and 20'000 milliPascal·sec, even more preferably between 1000 and 20'000 milliPascal·sec. The skilled person chooses materials, dimensions and tolerances in accordance with the viscosity of the fluid.

In other words, the instant disclosure teaches a cover 1, wherein the at least one seal 4 comprises a tip 5 and/or wherein the at least one seal 4 is configured to mate with a flat surface or with a reciprocating groove in an inner wall of a tubular housing 18 such that the arrangement becomes fluid-tight.

The tubular housing 18, the printed circuit board 20, and the cover 1 form basic elements of a duct sensor. It is envisaged that the duct sensor according to this enclosure meets the criteria for IP45, IP55, IP65 protection or higher.

It is envisaged that the inside of the tubular housing 18 is cast in a suitable potting compound. This step may typically be carried out when manufacturing a duct sensor. The potting compound eventually acts to protect electric and/or electronic components 21a, 21b inside the tubular housing 18. The potting compound may also function to improve on electrical insulation. Further, the potting compound may eventually protect the assembly against mechanical shock and ambient stresses such as ingress of fluids, in particular against ingress of moisture. By casting the inside of the tubular housing 18 into a suitable potting compound, the assembly may qualify for use in hazardous environments.

The skilled person chooses a suitable potting compound such as epoxy resins, polyester resins, (room temperature vulcanizing) silicone resins and any suitable combinations thereof. A potting compound may be chosen that cures at room temperature or at elevated temperatures. This list is by way of non-limiting example.

The skilled person considers the dimensions of the tubular housing when selecting a potting compound prone to heat shrink. The skilled person also selects a potting compound that is compatible with the material of the tubular housing 18 and is compatible with the material of the cover 1.

Figure 4:
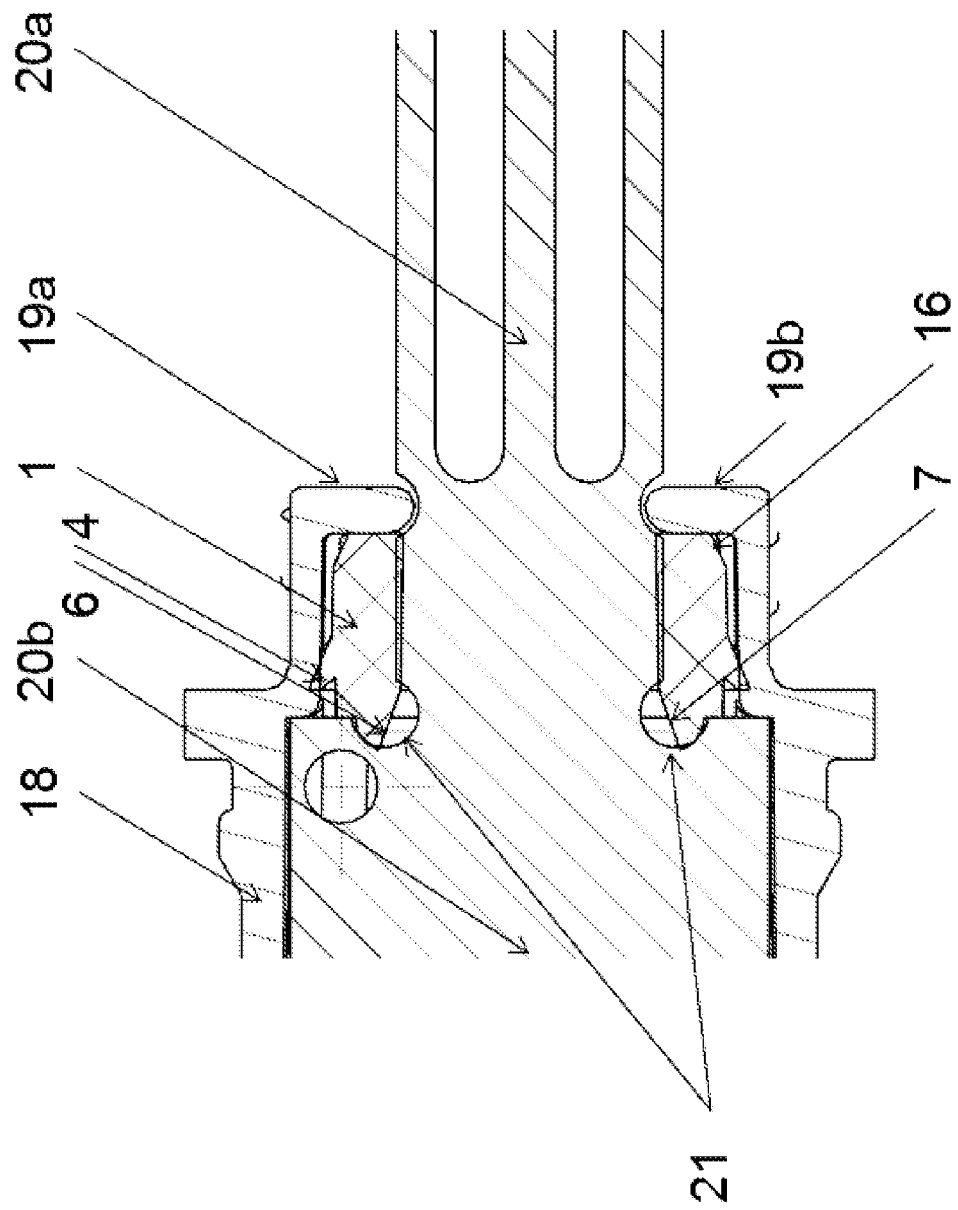
FIG. 4 is another cross-sectional view of an assembly comprising a tubular housing, the cover and a circuit board.

Now turning to FIG. 4, another cross-sectional view of the assembly of FIG. 3 is provided. The view of FIG. 4 is actually taken at an angle of 90 degrees compared to the orientation of FIG. 3.

FIG. 4 shows a (printed) circuit board 20 with sections outside 20a and inside 20b the tubular housing 18. The cover 1 separates the inside section 20b from the outside section 20a of the circuit board 20. It is envisaged that the outside section 20a of the circuit board may carry a humidity sensor such as a Sensirion SHT20 sensor, a Sensirion SHT21 sensor, Sensirion SHT25 sensor, a Si7005-B-GM1R sensor, a SI7015-A10-GM1 sensor, a Si7020-A10-GM sensor, a Si7021-A10-GM sensor, a Si7021-A10-GM1 sensor, a Si7005-B-FM1R sensor, a Si7013-A10-GM sensor, a Si7013-A10-GM1 sensor, or a Si7005-B-GM1 sensor available from Silicon Labs. The skilled person may as well select a temperature sensor such as a PT100, a PT1000, a PTC or a NTC sensor. These lists are by way of non-limiting example. The skilled person may also select other temperature and/or humidity and/or moisture and/or (atmospheric) pressure and/or light sensors.

It is envisaged that the end portions 19a, 19b of the tubular housing 18 mate with reciprocating lateral notches in the circuit board 20. In this embodiment, the lateral notches together with the end portions 19a, 19b define the position of the circuit board 20 with respect to the tubular housing 18. The end portions 19a, 19b and the reciprocating notches may, but need not ensure fluid-tightness of the arrangement. It is envisaged that fluid-tightness is primarily achieved through the cover 1. Without fluid-tightness between the end portions 19a, 19b and the reciprocating lateral notches, the corresponding technical constraints and tolerances may be relaxed to some extent.

The view of FIG. 4 also provides details of how the latching members 6, 7 latch onto lateral notches 21 along both sides of the circuit board 20. It is envisaged that each of the lateral notches 21 forms a sector of a circle. In alternate embodiments, the notches 21 may be shaped quadratic, rectangular, oval, triangular, or any suitable combination thereof.

The latching members 6, 7 thereby define the position of the cover 1 with respect to the circuit board 20. By the same token, the latching members 6, 7 and the end portions 19a, 19b define the position of the cover 1 with respect to the tubular housing 18.

In other words, the instant disclosure teaches a duct sensor comprising a tubular housing 18 with end portions 19a, 19b, a circuit board 20, and a cover 1 as detailed in this disclosure, wherein the cover 1 is mounted inside the tubular housing 18, wherein the circuit board 20 extends through the cover 1.

In other words, the instant disclosure teaches a duct sensor, wherein the end portions 19a, 19b provide inner surfaces and wherein the front surface of the cover 1 is flush with inner surfaces of the end portions 19a, 19b.

In other words, the instant disclosure teaches a duct sensor, wherein the cover 1 connects to the walls of the tubular housing 18 such that no uncured potting compound will leak in between the cover 1 and the tubular housing 18.

In other words, the instant disclosure teaches a duct sensor, wherein and the cover 1 connects to the circuit board 20 such that no uncured potting compound will leak in between the cover 1 and the tubular housing 18.

The instant disclosure also teaches an apparatus with at least a fuel cell and with at least a duct sensor according to the instant disclosure, wherein the at least a duct sensor is configured to monitor a physical quantity inside the fuel cell.

The instant disclosure also teaches an apparatus with at least a cogeneration plant and with at least a duct sensor to the instant disclosure.

The instant disclosure also teaches an apparatus with at least a cogeneration plant and with at least a duct sensor according to the instant disclosure, wherein the at least a duct sensor is configured to monitor a physical quantity inside the at least a cogeneration plant.

It should be understood that the foregoing relates only to certain embodiments of the invention and that numerous changes may be made therein without departing from the scope of the invention as defined by the following claims. It should also be understood that the invention is not restricted to the illustrated embodiments and that various modifications can be made within the scope of the following claims.

REFERENCE NUMERALS 1 cover
2 duct
3 outer envelope
4 seal
5 tip of the seal
6 latching member
7 latching member
8 tapered wall of the duct
9 top wall of the duct
10 front side of the cover
11 rear side of the cover
12 rectangular opening
12a, 12b lips of the rectangular opening
13a, 13b set of points delimiting a dimension of the rectangular opening
14 set of points delimiting a dimension of the rectangular opening
15a, 15b, 15c, 15d apertures
16 tapered end
17 guide runner
18 tubular housing
19a, 19b end portions of the housing 18
20 (printed) circuit board
21 lateral notches in the circuit board

What is claimed is:

1. A cover for a duct sensor, the cover comprising:
an outer envelope circumferentially surrounding the cover and connecting to at least one seal, the at least one seal projecting from the outer envelope and circumferentially surrounding the outer envelope;
at least one duct extending through the cover and defining a plurality of walls and including side walls, wherein the at least one duct comprises at least one guide runner laterally arranged along a side wall of the at least one duct;
a front surface between the outer envelope and the plurality of walls of the at least one duct;
an opening in the front surface that defines an entry for a circuit board into the at least one duct;
wherein the at least one guide runner is configured to support the circuit board extending through the duct;
wherein the at least one guide runner and the opening are configured to secure a circuit board extending through the duct and the opening includes at least one lip configured to mate with a reciprocating groove in a surface of the circuit board such that the arrangement becomes fluid-tight
wherein the at least one seal comprises a tip, and the at least one seal, the tip, the outer envelope, and the cover form a single integrated piece.

2. The cover of claim 1, wherein the opening is rectangular and/or wherein the width of the opening and/or the height of the opening are such that a circuit board may fit through the opening.

3. The cover of claim 1, wherein the at least one seal is configured to mate with a flat surface or with a reciprocating groove in an inner wall of a tubular housing such that the arrangement becomes fluid-tight.

4. The cover of claim 3, wherein the at least one seal and the tip and the outer envelope and the cover are made of the same material.

5. The cover of claim 3, wherein the outer envelope and/or the at least one seal and/or the tip all have cylindrical symmetry with respect to an axis through the at least one duct.

6. The cover of claim 1, wherein the at least one seal is resiliently yieldable so as to adapt to a groove on the inside of a tubular housing.

7. The cover of claim 1, wherein the at least one seal is an annular seal and/or wherein the at least one seal is configured to mate with an annular groove on the inside of a tubular housing.

8. The cover of claim 1, wherein the at least duct provides guide runners on either side wall of the at least one duct.

9. The cover of claim 1, wherein the opening provides at least one lip and the at least one lip is configured to snugly receive the surface of a circuit board such that the arrangement becomes fluid-tight.

10. The cover of claim 1, wherein a plurality of apertures are arranged in the front surface of the cover.

11. A duct sensor comprising:
a tubular housing including end portions;
a circuit board; and
a cover mounted inside the tubular housing, the cover comprising:
an outer envelope circumferentially surrounding the cover and connecting to at least one seal projecting from the outer envelope and circumferentially surrounding the outer envelope, wherein the at least one seal comprises a tip;
wherein the at least one seal, the tip, the outer envelope, and the cover form a single integrated piece;
a duct extending through the cover and including a plurality of walls and side walls, wherein the duct comprises at least one guide runner laterally arranged along a side wall of the duct; and
a front surface between the outer envelope and the plurality of walls of the duct;
wherein the circuit board extends through an opening in the front surface of the cover and through the duct;
the at least one guide runner of the cover supports the circuit board extending through the duct; and
the cover connects to the circuit board to prevent uncured potting compound from leaking between the cover and the tubular housing.

12. The duct sensor of claim 11, wherein the end portions of the tubular housing define inner surfaces, and wherein the front surface of the cover is flush with inner surfaces of the end portions.

13. The duct sensor of claim 11, wherein the cover connects to the walls of the tubular housing to prevent uncured potting compound from leaking between the cover and the tubular housing.

* * * * *